United States Patent [19]

Caron et al.

[11] 4,128,004

[45] Dec. 5, 1978

[54] METHOD AND APPARATUS FOR DETERMINING PERMEABILITY OF FILTER MEDIA

[75] Inventors: Jacques Caron, Courbevoie; Jean-Claude Poncet; Bernard Varney, both of Villers Cotterets, all of France

[73] Assignee: Société Anonyme dite: CECA S.A., Velizy-Villacoublay, France

[21] Appl. No.: 835,701

[22] Filed: Sep. 22, 1978

[30] Foreign Application Priority Data

Oct. 8, 1976 [FR] France ................................ 76 30351

[51] Int. Cl.² ............................................. G01N 15/08
[52] U.S. Cl. ................................................... 73/38
[58] Field of Search ............................................ 73/38

[56] References Cited

U.S. PATENT DOCUMENTS

| 2,392,637 | 1/1946 | Boehler | 73/38 |
| 2,401,122 | 5/1946 | Thoresen et al. | 73/38 |
| 2,745,057 | 5/1956 | Dotson | 73/38 |

*Primary Examiner*—S. Clement Swisher
*Attorney, Agent, or Firm*—Bacon & Thomas

[57] ABSTRACT

In the measurement of the permeability of a filter medium a cake of the medium is formed in a holder by supplying an excess of the medium, as a suspension under pressure, to the holder, the pressure being relieved and the excess portion being removed to leave an undried cake of medium when the excess portion has dried to a given level as sensed by a pair of electrodes. Two further electrodes are used to determine the time for a given volume of liquid to pass through the cake for measuring its permeability.

7 Claims, 4 Drawing Figures

METHOD AND APPARATUS FOR DETERMINING PERMEABILITY OF FILTER MEDIA

The present invention concerns a method and an apparatus for determining the permeability of filtering media.

These media are generally called, in the filtering art, filter cakes or media.

The filtration of suspensions of granular solids, such as particles of cellulose, kaolin, metallic hydroxides, carbon, plastics material, various minerals, dispersed in some kind of liquid — water being the one most used — through a filtering media, is a current problem in industry.

The filtration of suspensions of large solids is normally effected by grids, sheets or fabrics having relatively large openings.

When it is a question of the filtration of suspensions of particles of small dimensions, such as those of a clay, a filtering medium, such as a fabric, is not generally sufficient. The filtration has to be effected through a filtering medium with very fine pores generally constituted by a cake of a product known as a filtration aid, an inert, fine, light and porous substance which is disposed at some thickness on a permeable support surface known as a septum which may be a fabric.

The principal filtration aids are those of kieselguhr base and those of perlite base. Kieselguhr or diatomite is a rock constituted by skeletons of microscopic algae, the diatoma, which are to be found in the state of layers. A selection and activation treatment enables a fine powder to be obtained which leads to the formation of cakes of great porosity due to the particular form of the skeletons.

Perlite is a volcanic rock which, crushed into fine particles and heated, expands into the form of small hollow grains from which the crushing produces a light porous powder having the property of filtration aids.

There also exists other filtering media: sand, carbon, cellulose fibres, etc.. The filtration aids are normally used in two ways:

According to the first method, a dose of filtration aid, the most common in the form of sludge, in a concentration which more often is between 0.05 and 0.3% inclusive by weight, is incorporated in the total volume of the suspension to be treated. The filtration aid is deposited during the course of filtration at the same time as the impurities to be eliminated whilst forming with the latter a mixed cake the resistance to flow of which is considerably less than that which would have been provided by the cake of impurities alone.

This method is currently known as feeding or depositing.

According to a second method, a previous covering of filtering agent is provided on the septum so as to form a filter cake of appropriate thickness known as a pre-layer.

The flow of filtrate which in some way is a measure of the facility with which filtration is effected, depends on the area of filtration, on the pressure applied to the suspension to be filtered, on its viscosity and above all on the resistance opposed to the flow, on the one hand, by the septum chosen so as to combine efficiency and low resistance, on the other hand, and principally, by the deposit of the filtration aid constituting, from the beginning or progressively, the filter cake.

During filtration, it is necessary to know the ease with which filtration is effected. To do this, different methods can be carried out.

The currently most used method which employs depositing and thus leads to a progressive growth of the deposited cake, consists in measuring the volume of discharged filtrate as a function of time. The apparatus comprises essentially, a filter equipped with a septum, in the circumstances a fine metallic gauze, the filter being disposed within a container serving as a reservoir for the suspension to be filtered.

A given pressure is applied to the suspension, if needs be whilst ensuring agitation of the liquid by the gas maintaining the motive pressure.

In certain cases, the filter aids are compared or classified simply by comparing the volumes of discharged filtrate during a particular period under the conditions provided. This, which enables differentiation of the filter aids, does not, however, lead to the knowledge of values corresponding to a characteristic quantity of the filter cake, such as the resistance opposed by the latter to the discharge, or inversely, its permeability.

Nevertheless, this may be determined from the volume of filtrate discharged as a function of time, on condition that the discharge follows the usual laws of filtration whatever the thickness of the cake may be.

The permeability which is thus defined is generally the volumetric permeability with respect to unit area.

Another method consists in first of all depositing the cake, then measuring the volume of discharged filtrate under given conditions during a predetermined period.

In these conditions, the filtration law is a simple law normally termed the law of Darcy:

$$\frac{V}{t} = \frac{B \cdot S \cdot P}{\eta \cdot e}$$

where V is the volume of filtrate of a dynamic viscosity $\eta$ during the time t through the surface area S of the filtering medium, P is the motive pressure applied to the liquid at the level of the surface between the cake, e the thickness of the cake and B its volumetric permeability.

The volumetric permeability is currently expressed as Darcy.

The Darcy is the permeability of a medium 1 cm in thickness which, under a difference is pressure of 1 atmosphere, permits a flow of 1 $cm^3$ per second of a liquid of a viscosity of 1 centipoise to discharge through an area of 1 $cm^2$.

These methods of generally lengthy to carry out, requiring supplementary calculations, such as those of the volumetric mass of the cake is position and/or complex calculations, in particular for the first method cited.

The method and apparatus according to the invention, enables the measure of permeability to be arrived at directly within periods 5 to 10 times shorter than those of other methods. Moreover, the measures are particularly reproducible, repeatable and accurate.

Thus, the present invention concerns a method of measuring the permeability of filtering media, characterised in that:

(1) A cake is preformed by introducing under pressure into a cake holder of predetermined dimensions, a suspension of the filtering medium in a liquid, until the summit of the cake, not used for the said measurement, covers, at least in part, two measuring electrodes.

(2) The said electrodes are connected to an electrical circuit designed to cut off the pressure when the said summit attains a given degree of selected dehydration such that the remainder of the cake is not subjected to the commencement of drying.

(3) The said partially dried summit is removed and the measure of permeability is carried out on the cake having a maximum degree of moistening whilst causing the liquid to pass through the cake.

The cake holder comprises a septum.

The pressure exerted above the cake holder during the course of filtration may be produced by a compressed gas, preferably air.

Of course, an analogous means for exerting a pressure above the cake holder could consist in producing a vacuum below the cake holder.

Suspensions or sludges may be used having very high concentrations of filtering media up to many hundreds of g/l.

The electrical circuit for cutting off the pressure may comprise a Wheatstone bridge of which one of the resistors is constituted by the summit electrode assembly, that is the summit of the cake not used for measurement.

With the method in accordance with the invention, a predetermined volume of liquid having passed through the filtering medium during a predetermined period, is preferably measured.

This volume of liquid may, for example, be measured by two electrodes located at two different levels above the cake and immersed, at the commencement of measurement, in the filtration liquid.

The present invention also concerns an apparatus enabling the method in accordance with the invention to be carried into effect, characterised in that, it comprises a removable cake holder situated within a tube, means enabling a pressure to be exerted above the cake holder, means comprising electrodes for stopping the said pressure and means enabling a certain volume of liquid to be measured having passed through the cake during a predetermined period so as to estimate the permeability of the said cake.

By virtue of the method in accordance with the invention, a preformed cake of constant dimensions is produced and which is always at its maximum degree of humdity, having regard to the system of two electrodes disposed within the summit of the cake to be levelled.

The discharge of filtration liquid is effected through the preformed cake according to the simple law of Darcy under defined conditions of pressure and viscosity. Knowledge of the permeability is then reduced to the measurement, of either a volume discharged during a given period or a discharge time for a given volume, or of a discharge flow. Preferably, the period of discharge for a given volume is measured. In these circumstances, the permeability B is reduced to:

$$B = \frac{K}{t}$$

K being a constant integrating the constants of the apparatus, S and e, and the operating constants, P, V, η. These different constants are previously established as a function of the zone of permeability to be measured.

The method according to the invention leads to the direct knowledge of the permeability at a speed of 5 to 10 times faster than that of the other methods and with an improved accuracy.

The present invention will be better understood by reading the following examples given by way of example and in no way limiting, reference being made to the accompanying drawing in which.

Figure 1:
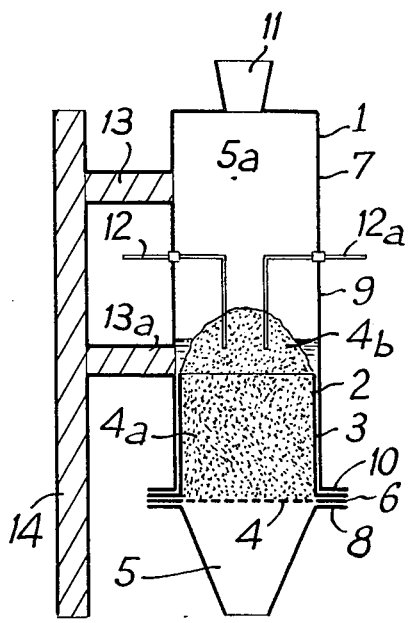
FIG. 1 is a diagrammatic section of a cake forming apparatus.

In FIG. 1, it can be seen that a cake forming apparatus is constituted by a cake holder 2 formed by a cylinder 3 having a septum 4 as a base on which is deposited the constituents of the cake in the form of powder 4a. Below the said base, the cylinder 3 is extended as a cone 5 situated beneath the cylinder 3 collecting and evacuating the filtrate 5a. Moreover, at the level of the said base, it comprises an external collar 6.

Formation of the cake is produced by means of a tube 7 called the formation tube. The cake holder is situated on a support 8 where it rests by means of its collar 6 and the assembly is surmounted by the formation tube 7 for the cake constituted by a cylinder 9 having a collar 10 at its base which rests on the collar 6 and has a funnel 11 at its summit. The tube 7 serves as a support for the two electrodes 12 and 12a.

The tube 7 is fixed, through the agency of two arms 13 and 13a, to a rod 14 operated by an electro-pneumatic system. An electro-hydraulic system or a mechanical system could also be used provided that it produced the same result, that is to say, that it enabled a fluid-tight contact between the collars 6, 8 and 10 to be ensured, as in the position of FIG. 1.

The electrodes 12 and 12a are connected to a system so that, at the opportune moment, it controls the stopping of the formation of the cake.

For this operation of cake formation, the tube 7 is filled from the top with a suspension of the filtration aid to be tested and a pressure is applied, for example by means of a compressed gas especially air, by placing the funnel 11 in communication with a fluid-tight system for supplying gas, or, by closing the funnel 11 in a fluid-tight manner and supplying the compressed gas through an orifice in the upper part of the tube. Another way of exerting the pressure is to produce the vacuum through the bottom of the cone 5.

Under the effect of the pressure, the filtration aid is deposited on the septum 4 at the base, the filtrate discharges through the cone 5. At a given moment, the cylinder 3 is filled and the filtration aid accumulates whilst forming a summit or dome known as a mushroom 4b which engulfs the ends of the electrodes 12 and 12a, the quantity of filtration aid used having been largely evaluated so that it would form a sufficient mushroom but without excess.

When the whole of the suspension is filtered, the mushroom or summit surmounting the cake is partially dried or drained by the discharge of the interstitial liquid, its electrical conductivity diminishes, the electrical resistance between the electrodes 12 and 12a increases and through the agency of an adequate circuit, cuts off the current controlling the pressure and if needs be, acts on an electro-pneumatic control system for disengaging the cake holder 2 from the tube 7. The position of the electrodes 12 and 12a is such that the cake which will serve for the measurement as such is not subjected to any initial drying.

One of the means for releasing the cutting off of the pressure consists in considering the mushroom electrode assembly as one of the resistors of a Wheatstone bridge.

Figure 2:
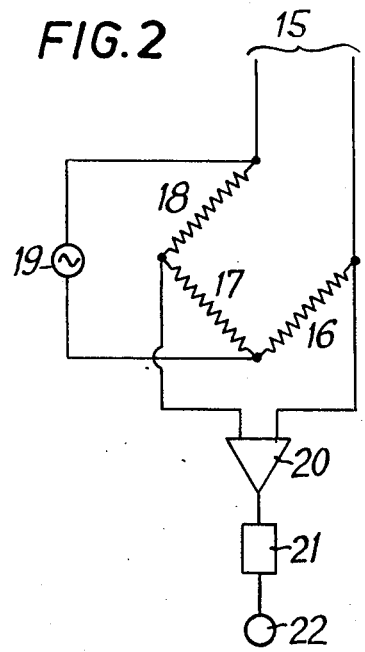
FIG. 2 is an electrical circuit diagram of the two electrodes immersed in the summit of the cake.

FIG. 2 is a diagram of a device which could be used. The electrode mushroom assembly constitutes the resistor 15, the resistors 16 and 17 are preferably of equal value and in that case the resistor 18 has the same value R as that of the electrode mushroom assembly 15 at the instant when it is desired to cut off. The bridge is supplied from a source of alternating current 19 and the output signal connected to an amplifier 20, a relay 21 and a control system 22.

The electrical conductivity of the suspension is such that the electrical resistance is low and lower than that of R of the resistor 18. When the mushroom has been formed and starts to dry, the electrical resistance increases substantially and when it attains the value R the amplifier 20 acts on the control system 22, shuts off the pressure, thus stopping the formation of the cake and if needs be, acting so as to disengage the cake holder 2 from the tube 7.

The use of the Wheatstone bridge system, based on the variation in electrical conductivity, is one of the preferred means of the invention, however, means based on the variation in capacity, specific field strength, etc., may also be selected and electronic systems such as monostable gates, rearming threshold detectors or combinations of these systems may be used.

The cake holder 2 having been disengaged, it is levelled parallel to its upper base and the mushroom is thus removed. It has been noted that if the cake is formed under the conditions previously described, levelling is carried out without modification of its characteristics. The preformed cake of determined dimensions is then ready for the following stage.

Figure 3:
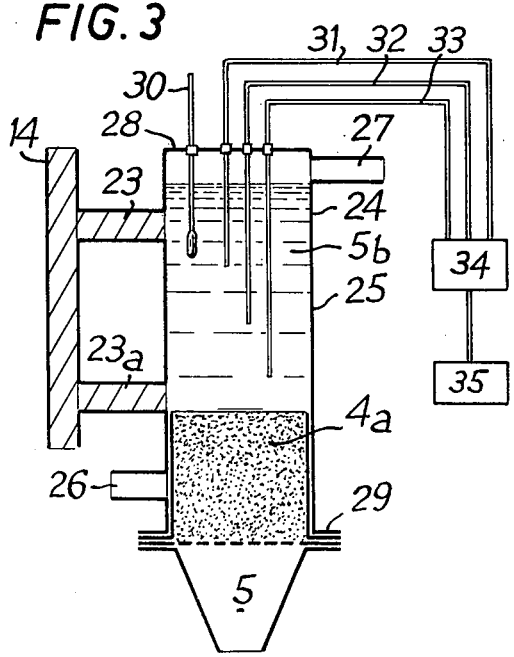
FIG. 3 is a diagrammatic section of an apparatus for measuring the permeability as such.

The operation of measuring permeability may be followed by means of FIG. 3.

The rod 14 of the electro-pneumatic system also supports the measuring tube by means of two arms 23 and 23a. By pivoting the assembly, the measuring tube 24 is brought into the position of the tube 7 for forming the cake.

The measuring tube comprises cylinder 25 having an inlet 26 for liquid 5b at its base and an overflow 27 at the top. The tube is closed at its upper part 28 and carries at the lower part a collar 29. A thermometer 30 enables the temperature of the liquid to be measured. Three electrodes 31, 32 and 33 are immersed inside the tube and are connected by a relay 34 to the control of an electronic chronometer 35. In this instance, it is preferred to measure the time necessary for the discharge of a given volume of liquid.

For measuring, the cylinder 25 is filled through the inlet 26, generally with water until there is a discharge through the overflow 27, in an appropriate manner so that the liquid filling does not modify the cake to be tested in any way. The inlet 26 and the overflow are closed and a gas under a given pressure, normally compressed air, is applied to the surface of the liquid. Instead of operating under pressure, suction can also be used through the base of the cone 5 in which case the overflow 27 is not closed.

During discharge of the liquid through the preformed filter cake, the moment arrives when the electrode 31 is no longer in contact with the liquid, and the operation of the electronic chronometer is initiated. When the liquid is no longer in contact with the electrode 32, the electronic chronometer is stopped and pressure is cut off. The position of the electrodes 31 and 32 defines the volume of liquid discharged in a measured period.

Instead of electrodes, equally sensitive interface elements, capacitive, dielectric, and even radio-active, could be used.

The resetting of the chronometer to zero is effected automatically on filling.

The method such as described, comprises certain manual operations but it can be used by producing the series of operations automatically:
 production of the suspension
 setting up of the cake forming tube
 filling and forming of the cake
 removal of the cake forming tube
 positioning the measuring tube
 filling
 measuring
 removal of the measuring tube.

From the time t measured on the electronic chronometer, the measurements being carried out at a known or constant temperature, a simple calculation carried out in accordance with the formula referred to above, provides the permeability. By introducing the signal from the electronic chronometer into a simple calculation circuit, the linear permeability in Darcy can be displayed and read off directly.

Figure 4:
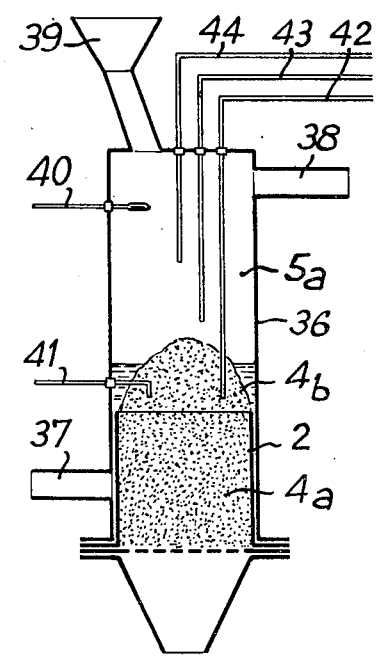
FIG. 4 is a diagrammatic section of a combined apparatus providing formation of a preformed cake and the measurement of permeability.

The method may be used with another embodiment of the apparatus according to FIG. 4.

In FIG. 4, a single tube 36 serves for the formation of the cake and also for measuring. The apparatus comprises the cake holder 2 and the tube 36 which is provided with an inlet 37, an overflow 38, a charging funnel 39, a thermometer 40 and four electrodes 41, 42, 43 and 44.

The electrodes 41 and 42 come into play for stopping the cake forming pressure, the electrodes 41 and 44 for starting the chronometer and the electrodes 41 and 43 for stopping it. The apparatus comprises the same accessories as the apparatus previously described and the operation may be controlled automatically.

Three examples of use are given hereafter.

EXAMPLE 1

A cake holder having the following characteristics is used:
 inner diameter : 3.90 cm
 useful height : 5.00 cm
The apparatus is designed for a volume of liquid to be filtered of 61.2 cm$^3$.

20 g of a perlitic filtering agent are dispersed by manual agitation in 200 ml of water. Agitation is just enough to properly disperse the product and to maintain it in an homogeneous suspension. The whole of the suspension is introduced into the cake holder and filtration under a motive pressure controlled at 0.8 atmospheres is commenced. When filtration is terminated, the cake forming tube is raised, the cake levelled with a rule, the edges of the cake holder cleaned rapidly. The measuring tube is mounted on the cake holder, and water is introduced into the measuring tube. This operation having been done, filtration of the water under motive pressure regulated at 0.8 atmospheres is started. The measured time is 25.5 seconds. The temperature of the water during the course of the test is 21.0° C. (corresponding viscosity : $\eta = 0.981$ centipoises).

The coefficient K of the apparatus being 31.43, the permeability is:

$$B = \frac{31.43}{25.5} = 1.23 \text{ Darcy}$$

EXAMPLE 2

With the same apparatus as in example 1, 40 g of a diatomitic filtering agent is dispersed in 200 ml of water under the same conditions.

The temperature during the course of the test is 19.8° C. (corresponding viscosity : $\eta = 1.010$ centipoises).

The measured time is 44.2 seconds
The coefficient K is 32.46
The permeability is B = 0.735 Darcy.

A series of 11 consecutive measurements have been effected on the same product by an experimental very little used to the apparatus. The average figures obtained corresponded to 0.738 Darcy and there was a deviation of the order of 0.0106.

For 5 different experiments, the average was also 0.738 Darcy and the kind of deviation 0.0138.

The total duration of a test was on the average 4 minutes 15 seconds.

EXAMPLE 3

Operations were carried out under the following conditions:

| | | |
|---|---|---|
| inner diameter of the cake holder | 3.90 | cm |
| useful height of the cake holder | 2.20 | cm |
| volume of water to be filtered controlled at | 17.63 | cm$^3$ |
| motive pressure | 0.8 | atmospheres |

Under the same conditions as previously, 20 g of diatomitic filtering agent is dispersed in 100 ml of water.

The temperature of the water is 20.5° C. (corresponding viscosity : $\eta = 0.993$ centipoises).

The coefficient K is 4.03.

The permeability is B = (4.03/60.4) = 0.067 Darcy

These examples as well as the description of the apparatus have been established with the use of filtration aids.

However, the method is not limited to this use. It is also applicable to all solid granular cakes. The cake holder may also be modified so as to be adapted to the measurement of septum or membrane permeability.

What is claimed is:

1. In a method of measuring the permeability of a filtering medium by passing liquid through a cake of the medium, the improvement which comprises preforming a cake by:

introducing into a cake holder of predetermined dimensions a suspension of the medium in a liquid, the suspension being introduced under pressure, a pair of electrodes being located above a predetermined level of the medium in the cake holder;

terminating said introduction of the suspension when a portion of the medium above said predetermined level at least partially engulfs said electrodes while continuing to apply said pressure;

Interrupting said pressure when said portion of medium attains a predetermined degree of dehydration as sensed by electrical means including said electrodes, the remainder of the media not being subjected to any drying; and removing said partially dried medium portion to leave a cake of medium of predetermined dimensions and maximum moisture content through which the liquid is passed to measure the permeability of the medium.

2. The method of claim 1, wherein said pressure is applied by applying suction beneath the cake holder.

3. The method of claim 1, wherein said pressure is applied by causing compressed air to act above the cake holder.

4. The method of claim 1, wherein said electrical means comprises a Wheatstone bridge and said electrodes define a resistor forming one of the branches of said bridge.

5. The method of claim 1, including measuring the time for a predetermined volume of liquid to pass through said cake.

6. The method of claim 5, wherein said time is sensed by two electrodes located above the cake of medium.

7. Apparatus for measuring the permeability of a filtering medium, comprising:

a filter cake holder and a tube surrounding said holder;

means for introducing a liquid suspension of filtering medium into said tube and holder;

means for applying pressure to said liquid;

a pair of electrodes above the filtering medium in said cake holder;

means responsive to accumulation of filtering medium in said holder up to a level at least partially engulfing said electrodes for terminating introduction of said suspension whereby said liquid passes through said medium;

means responsive to at least partial dehydration of only said medium between said electrodes, as detected by said electrodes, for terminating application of said pressure whereby said portion of said medium engulfing said electrodes may be removed to leave a cake of predetermined dimensions and maximum moisture content; and means for sensing the subsequent passage of a predetermined volume of a liquid through said filter cake, as a measure of the permeability of the cake.

* * * * *

UNITED STATES PATENT OFFICE
CERTIFICATE OF CORRECTION

Patent No. 4,128,004     Dated December 5, 1978

Inventor(s) Jacques CARON, Jean-Claude PONCET and Bernard VARNEY

It is certified that error appears in the above-identified patent and that said Letters Patent are hereby corrected as shown below:

On the title page, the line preceding the claim for priority should read --Filed September 22, 1977.

Signed and Sealed this

Twenty-fourth Day of April 1979

[SEAL]

Attest:

RUTH C. MASON
Attesting Officer

DONALD W. BANNER
Commissioner of Patents and Trademarks